United States Patent [19]

Nenov et al.

[11] Patent Number: 5,490,851
[45] Date of Patent: Feb. 13, 1996

[54] METHOD AND APPARATUS FOR TREATMENT OF IDIOPATHIC SCOLIOSIS

[76] Inventors: Nikolay N. Nenov, 6404 St George Street, Vancouver, B.C., Canada, V5W 2Y6; Orlin Nedelchev, 602 - 1040 Pacific Street, Vancouver, B.C., Canada, V6E 4C1

[21] Appl. No.: 284,944

[22] Filed: Aug. 2, 1994

[51] Int. Cl.$^6$ ............ A61B 17/70; A61B 17/60; A61B 17/56
[52] U.S. Cl. ............ 606/61; 606/54; 606/60
[58] Field of Search ............ 606/53, 54, 55, 606/56, 57, 58, 59, 60, 61, 69, 70, 71

[56] References Cited

U.S. PATENT DOCUMENTS

| | | |
|---|---|---|
| 2,333,033 | 6/1943 | Mraz ............ 606/59 |
| 4,112,935 | 9/1978 | Latypov et al. . |
| 5,084,049 | 1/1992 | Asher et al. ............ 606/60 |
| 5,105,489 | 4/1992 | Meyer . |

*Primary Examiner*—Stephen C. Pellegrino
*Assistant Examiner*—Scott B. Markow

[57] ABSTRACT

Apparatus to treat scoliosis, particularly idiopathic scoliosis. The apparatus has a pair of longitudinal struts whose separation can be adjusted. The cross member is pivotally attached to each strut. The apparatus can be secured to a patient's pelvic girdle. The cross member can be pivoted and thus move the patient's sacrum towards the innominate bones. The apparatus also provides a method to treat scoliosis in a patient that comprises repositioning the patient's sacrum to correct the anatomical position to restore the symmetry of the patient's pelvic girdle. The patient's sacrum is stabilized in its restored position by locating the sacrum to the iliac bone. The non-deformed vertebrae in the scoliotic curve is pulled by members attached to the ilium extending to the vertebrae procesus. The members are tensioned as required.

7 Claims, 3 Drawing Sheets

METHOD AND APPARATUS FOR TREATMENT OF IDIOPATHIC SCOLIOSIS

FIELD OF THE INVENTION

This invention relations to an apparatus to treat scoliosis.

DESCRIPTION OF THE PRIOR ART

Scoliosis is broadly defined as abnormal lateral curvature of the spine. Scoliosis disfigures a person but also can cause disfunction of some internal organs, for example the lungs and heart.

There have been a number of suggestions in the prior art to alleviate and, indeed, cure the condition.

Included in the prior art is an apparatus known as a distracter, which resembles a jack. The distracter has two rods. One end of each rod is divided into limbs and the other end is threaded. The rod is interconnected by a cylindrical tube having a two-way thread in the manner of a turnbuckle.

The split limbs are positioned on the bases of the vertebrae, at the base of the scoliotic arch and the sleeve is then screwed to the maximum. It is believed that this distracter has a corrective force of low efficiency. The force is applied to the spinal column during surgery and it cannot be altered while the distracter is in use. It has also been observed that the distracter may cause complications and can even fracture the transverse procesus of the vertebrae. Patients are bedridden for a long time with this technique and the distracter can only be removed by a second surgical operation.

A similar method of correcting scoliosis comprises the use of two metal rods with bent ends and straight ends. The straight ends are linked by a threaded sleeve. The bent ends are attached to the transverse procesus of the vertebrae on the convex side of the scoliotic arch. The sleeve is rotated and the contractor pulls at the transverse processes, thereby correcting the curvature of the spinal column. Again, there are divided limbs pressing against the transverse processes of the vertebrae. The slackening or unwinding of the sleeve extends the distracter. This straightens the curvature of the spinal column.

Although this latter method is preferred to the first, the contractor and the distracter permit correction of the curvature of the spinal column only during surgery. There is no subsequent improvement. The danger of fracturing the transverse procesus of the vertebrae also remains. Again, patients are bed-ridden for a considerable time and surgery is required to remove the device.

Steel springs have also been used. The ends of a spring are fixed on the transverse procesus of the vertebrae on the convex side of the scoliotic curvature. The spring acts as a contractor for a long time. This spring technique is generally considered superior to the two previous techniques but still has disadvantages. Again, the possibility of fracture exists and again the patient is bed-ridden. A surgical procedure is again required to remove the spring.

Skeletal traction of the spinal column has been used. The apparatus useful in this technique has two rings, at the head and at the pelvis. The rings are inter-connected by four expansion rods. The apparatus is applied by attaching metal pins through the iliac bones of the pelvis, secured in the pelvic ring. Four metal pins are inserted in to the cranium and are fixed to the head ring. By gradually unwinding the sleeves of the extended rod between the pelvic and head rings, longitudinal traction of the spinal column by the pelvic bone and the bones of the cranium is effected.

This method has relatively slight effect. With thoracic and lumbar scoliosis the traction produces a considerable traumatic effect on the cervical region of the spinal column, which has weak ligaments, but only a slight corrective effect on the curvature of the thoracic and lumbar regions. Neurological disorders are also possible as a result of traumatizing the nerves of the cervical region of the spinal column. It is also generally undesirable to introduce metal pins into the cranium in child-hood when the cranium is not properly formed. Obviously the external rings, surrounding the head and pelvis, prevent the patient from using an ordinary bed so that special equipment is required.

A technique similar to the above is the use of a head ring, again located by the use of cranial pins. The outer ends of the pins are fixed on the head ring. The upper ends of metal stay rods are fixed to the head ring. The lower ends are embedded in a cast, typically of plaster of paris. The rods are gradually extended by expansion sleeves, to effect traction of the spinal column.

An apparatus for the external traction of the spinal column is also known. This apparatus has a supporting shaft with L-shaped end feet at right angles to the shaft. There are disc resting on the tips. A third foot, which is also L-shaped and has a disc on the tip, is attached to the middle of the shaft in the direction opposite to that of the end feet. This apparatus is mounted alongside the spinal column of the patient. The three discs rest upon the patient's back. Nylon threads are attached to the processus of the three vertebrae, at the apex of the curvature of the spine and at the two bases. These threads are brought through the soft tissues in the skin of the back and are secured to the appropriate foot of the apparatus and tightened. In this way, the curvature is drawn from its apex towards the concave side and from the extreme vertebrae, towards the convex side.

Again, there are drawbacks. The apparatus is not fixed to the patients trunk but rests on three feet on the skin of the patient. This can be unstable. Use of the apparatus over any length of time may result in sores under the feet of the apparatus. The apparatus prevents the patient from rising which is clearly a disadvantage. Furthermore, the corrective force is not continuous.

U.S. Pat. No. 4,112,935, issued in September of 1978, describes an apparatus for surgical treatment of scoliosis in which a framework is formed by parallel struts secured at the ends by yokes and fixed on the patient's body by a system of belts. The belts are connected to the stay rods and fastened to the struts. Flexible braces serve to exert a corrective force on the vertebra. One end of each flexible brace is attached to the vertebrae and the other is a mechanism for applying varying tensions to the flexible braces.

The apparatus of the above United States Patent is believe to provide a risk of facilitating infection in a patient. The outside structure makes it difficult for a patient, for example movement is inhibited. Furthermore, the apparatus applies force only to the spine and it is applicant's position that this is not an adequate approach to the problem.

A further, relatively uncomplicated apparatus is described in U.S. Pat. No. 5,105,489 to Meyer issued Apr. 21, 1992. In that patent a device and method of treating scoliosis uses a seat cushion made up of two members having angled top surfaces. The two members are arranged in an opposed side-by-side position. To use the apparatus the innominate bones and the entire pelvic girdle of a patient seated on the seat cushion are tractioned into an opposing configuration through application of torque thereto by the tilting.

SUMMARY OF THE INVENTION

The present invention seeks to provide improvements over the prior art. It is believed to provide better results and is based on an analysis of the origins of idiopathic scoliosis. It is applicant's contention that the root of the problem is in the pelvic girdle and that the curvature of the spine results from displacement of the pelvic girdle.

Accordingly, the present invention provides an apparatus to treat scoliosis comprising a pair of longitudinal struts; means to adjust the separation of said struts; a cross member extending between said struts and pivotally mounted to each strut; means to secure said apparatus to a patient's pelvic girdle; means to pivot said cross member and thus move the patient's sacrum towards the innominate bones.

In a further aspect, the invention is a method to treat scoliosis in a patient that comprises repositioning the patient's sacrum to correct the anatomical position and to restore the symmetry of the patient's pelvic girdle, stabilizing the patient's sacrum in its restored position by locating the sacrum to the iliac bone; pulling the vertebrae in the scoliotic curve by members attached to the ilium and extending to the vertebrae transverse procesus; and tensioning the members as required.

DESCRIPTION OF THE PREFERRED EMBODIMENTS

Figure 1:
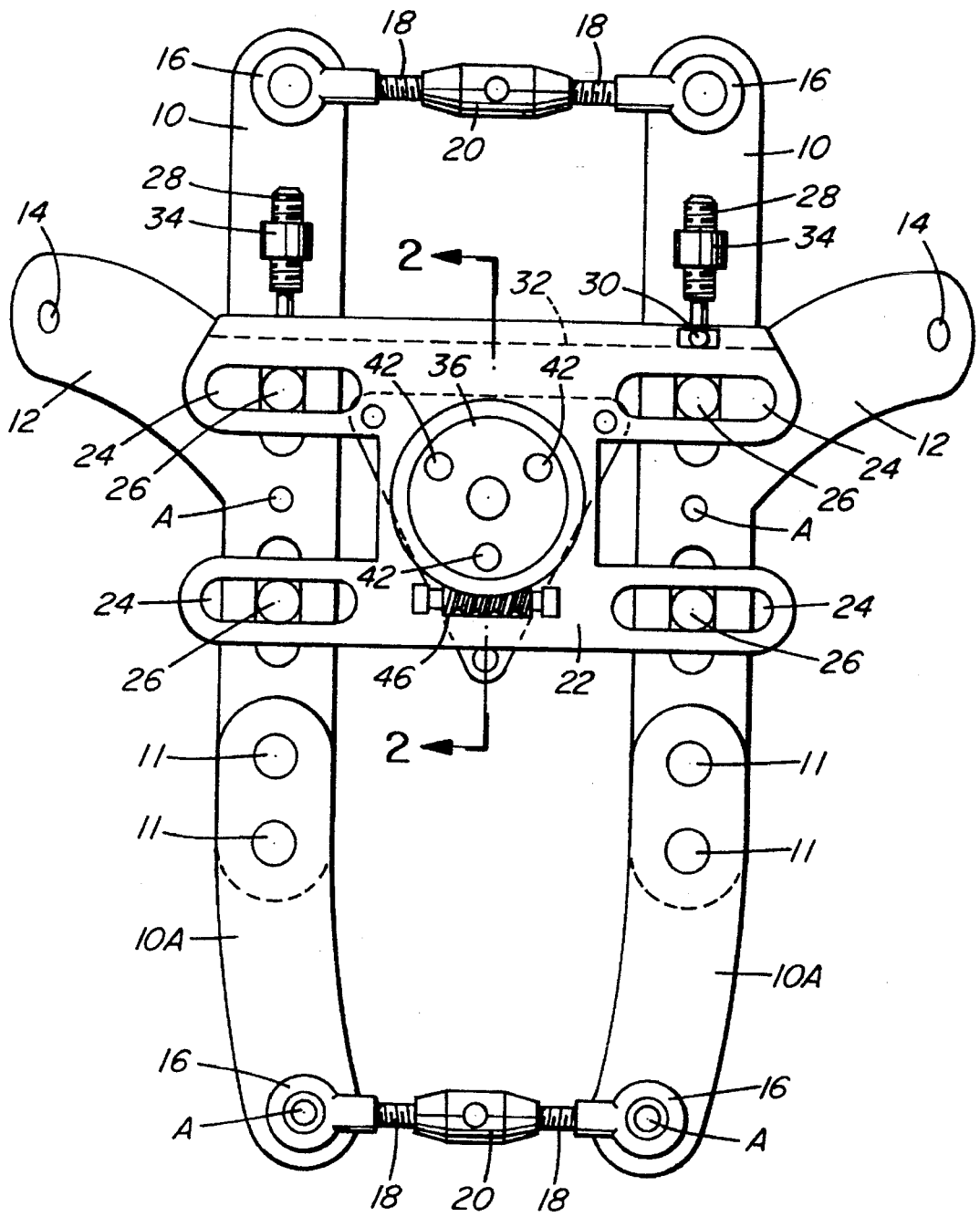
FIG. 1 is a front view of the apparatus of the present invention.

The drawings show an apparatus to treat scoliosis. The main apparatus comprises a pair of longitudinal struts 10 spaced from each other. These struts are designed to be attached to the ilium at points A. Side members 12 extend from the longitudinal struts, provided with openings 14 again to allow attachment to the ilium.

There are means to adjust the separation of the struts 10. This means comprises pivotal joints 16 at each end of the strut 10 and a turnbuckle made up of threaded members 18 extending inwardly from the pivotal joints 16 and is an internally threaded nut 20 that engages on the threaded studs 18. The studs 18 in each pair are oppositely threaded with regard to the other stud of the pair, so the rotation of the nut 20 in one direction either extends or contracts the stud length, thus acting to increase or decrease the separation of the longitudinal struts 10. There is a cross-member 22, generally H-shaped, extending between the struts 10. Member 22 is pivotally mounted to each strut 10. Member 22 has openings 24 adjacent each end. There are pins 26 in the longitudinal struts 10 that are pivotally received in the openings 24 in the cross-members 22. Nuts (not shown) are engaged on these threaded pins 26 to retain the cross-member 22 in position on the struts 10.

The cross-member 22 is also attached to the longitudinal struts 10 by longitudinally extending threaded members 28 engaged, by ball joints 30, with a channel 32 in the cross-member 22. These threaded members are also engaged in nuts 34, attached to the longitudinal struts 10.

Figure 2:
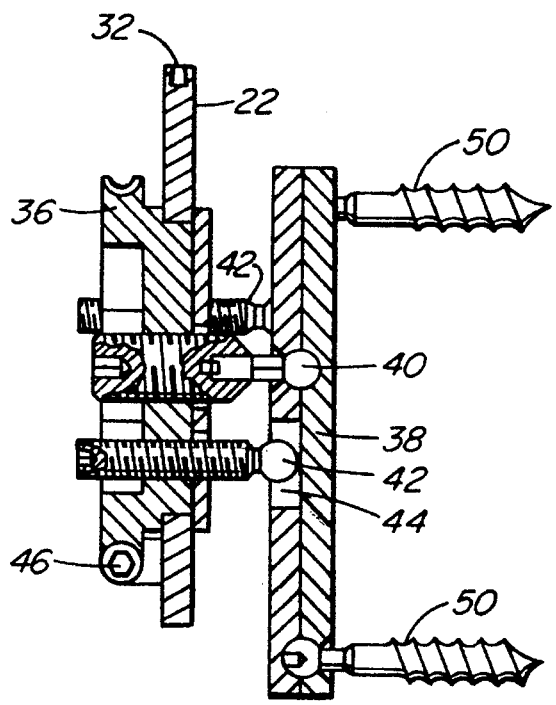
FIG. 2 is a section on the line 2—2 of FIG. 1.

As shown particularly in FIG. 2, there is a means to pivot the cross-member 22 relative to the longitudinal struts 10 comprising means to pivot the a wormwheel 36 attached to the cross-member 22. Wormwheel 36 and cross-member 22 are mounted on a sub-frame 38 by a central ball joint 40 surrounded by three ball joints 42 attached to the sub-frame 38 in openings 44 that permit their movement in the sub-frame 38.

There is a drive screw or worm 46, mounted on the cross-member 22 and engaging the wormwheel 36, which has an external track to engage screw 46. There are drive members at each end of the screw 46.

The longitudinal struts 10 are desirably formed in two parts. There are bottom parts 10A that may be detached from the upper portion at joints 11.

Figure 3:
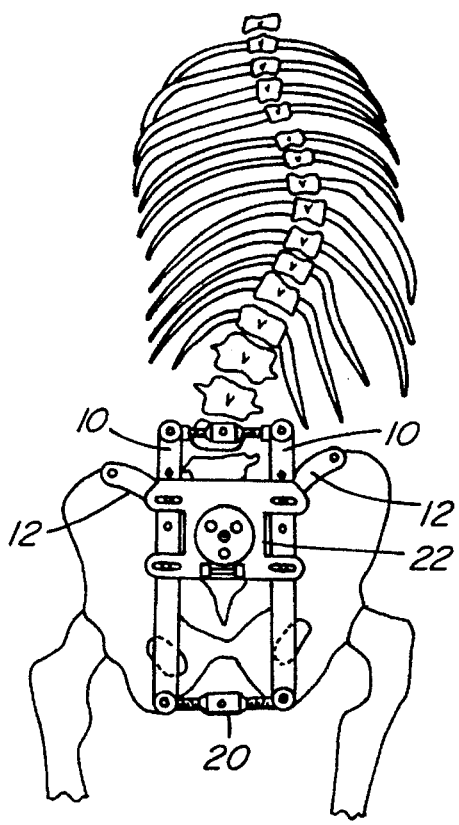
FIG. 3 illustrates use of the apparatus of FIG. 1.

To use the apparatus of FIGS. 1 and 2 the apparatus is attached, by a surgical procedure, to the skeleton of the patient in the position shown in FIG. 3. The longitudinal struts 10 are attached to the ilium and ischium and the cross-member 22 is attached to the sacrum by its attachment to sub-frame 38.

Adjustments are made, particularly to the studs 18 and to the openings 24 to position the apparatus of FIG. 1 on the patient. The nuts 20 may be used not merely to adjust the size of the device but also to assist in separating bones by applying a slight force. In particular the nuts 20 may be used to separate the innominate bones from the sacrum. Similarly the screws 28 may be rotated in the nuts 34 to "custom fit" the device to the patient also to apply a slight force as required.

The screws 50 used, are standard in orthopaedic surgery and are attached using conventional procedures in that art.

Once the device is in position, the shaft 46 is rotated. This rotates the wormwheel 36, mounted on the cross-member 22. This action pivots the sub-frame 38. By this means the longitudinal struts 10 and the cross-member 22 are pivoted relative to each other to apply a force to the pelvic girdle of the patient.

It is strongly recommended that muscle and ligament relaxants be given to the patient for some time prior to treatment to facilitate the movement of the bones. Such muscle and ligament relaxants are known in the art.

The bottom parts 10A may be removed, and usually will be removed, immediately after the repositioning or correction in the positioning of the pelvic girdle of the patient. The remainder of the apparatus may be left in place in a patient for at most one month subsequent to the operation but it may be removed immediately at the end of the operation. This is believed to be feasible in 90% of cases. Once the position of the pelvic girdle has been repositioned, computer tomography (CMT) is used to determine the position of the patient's sacrum. That is to say, the CMT will be used to determine that the pelvic girdle is restored to a correct, symmetrical position.

Figure 4:
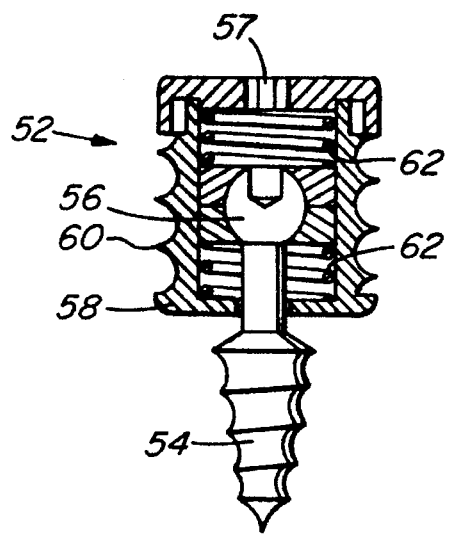
FIG. 4 is a section through an artificial joint useful in the method of the present invention.
Figure 5:
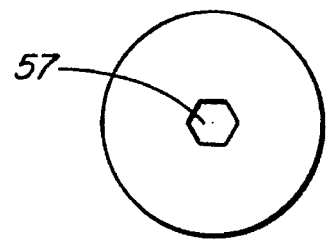
FIG. 5 is an end view of the artificial joint of FIG. 4.
Figure 6:
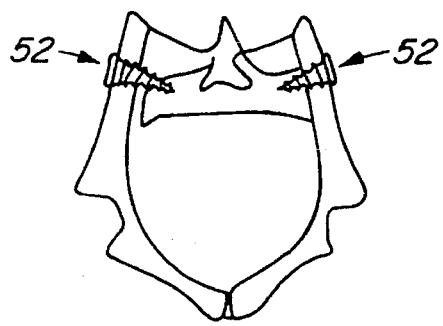
FIG. 6 illustrates the use of the joint of FIGS. 4 and 5.

FIG. 4 illustrates an artificial joint useful with the apparatus of FIGS. 1 to 3. As indicated above the apparatus of FIGS. 1 and 2 is intended for short term, and quite possibly very short term use. It is the function of the artificial joint shown in FIG. 4, which is mounted behind the sacroiliac joints and around the central sacroiliac ligament, as indicated in FIG. 6, to hold the repositioned sacrum pelvic girdle, repositioned that is by the apparatus of FIGS. 1 and 2. In contrast to the apparatus of FIGS. 1 and 2, the artificial joint of FIGS. 4 and 5 may be used to hold the position for a few years. It is used after treatment with the apparatus of FIGS. 1 and 2.

The artificial joint of FIG. 4 comprise a main screw member 54 to be received in the ilium. The screw 54 is provided with a slotted head 56 so that it can be engaged by a driver. The joint 52 is provided with an opening 57 to permit the insertion of a driver, and a hexagonal key configuration is shown, to drive the screw 54. The screw member 54 is received within housing 58 having a thread 60 that engages the sacrum. Springs 62 permit movement in the manner of a normal, natural joint. This is particularly desirable in the case of any artificial joint and does not inhibit natural growth.

FIG. 6 illustrates the position of the joints 52. Used in this manner, the joints 52 are able to retain a repositioned pelvic girdle in position. Frequently the apparatus of FIGS. 1 and 2 need not be left in position subsequent to the operation.

Figure 7:
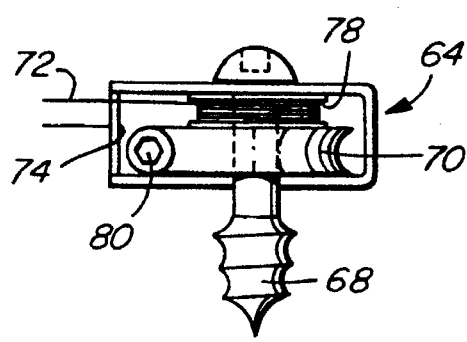
FIG. 7 is a side elevation of auxiliary equipment useful with the apparatus of FIG. 1.
Figure 8:
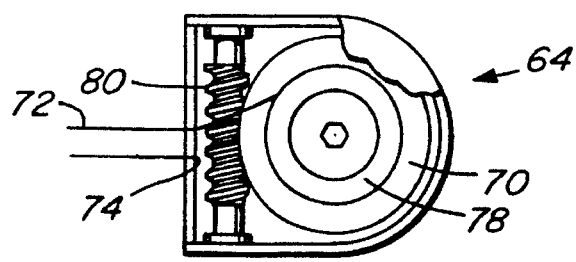
FIG. 8 is a plan view of the apparatus of FIG. 7.
Figure 9:
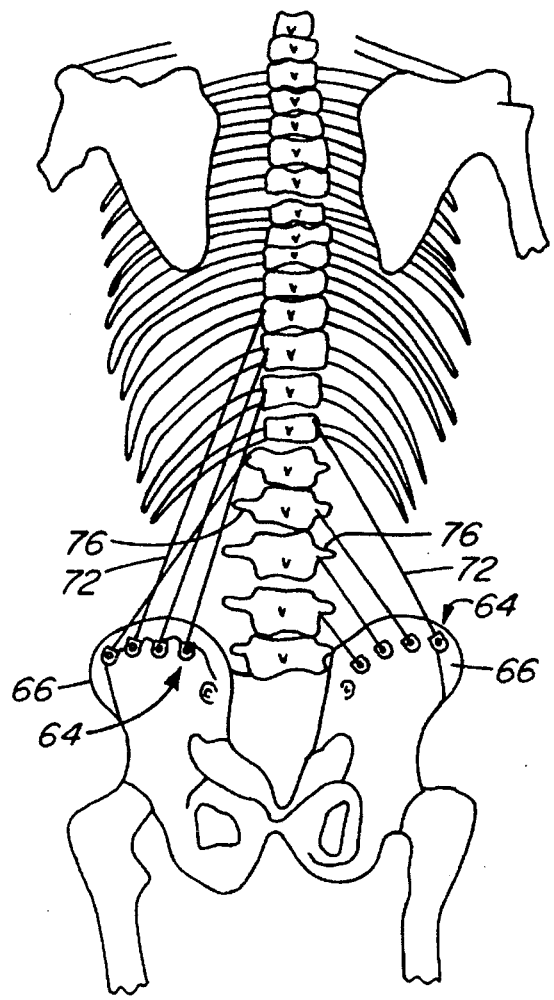
FIG. 9 illustrates use of the auxiliary equipment of FIGS. 7 and 8.

FIGS. 7, 8 and 9 show drive members 64 that can be mounted on the iliac crests 66 using a central screw 68. The positions are shown in FIG. 6. Again, a wheel 70 is provided and a flexible cord 72, for example of nylon, extends from a fixed point 74 on the drive member 64, outwardly to engage the vertebrae at 76, and down back onto a reel 78 attached to the wheel 70. An appropriate number of drive members 64 (eight are shown in FIG. 9) are mounted on the iliac crests 66 and tensioned appropriately by use of a screw 80. Quite sensitive control can be achieved with the simple and drive members 64 shown. These flexible cords 72 apply corrective force to the vertebrae. Desirably they can be hooked around the transverse procesus of the vertebrae during a first, main operation. Their removal can then be relatively simple. The appropriate incisions are made and the drive member 64 is removed. The cords 72 may be cut and removed from the vertebrae simply by pulling at the incision made to remove the drive mechanism.

Thus the apparatus of the present invention provides a simple, light-weight mechanism to cure scoliosis. A particular advantage of the device is that it does not have a major impact on the life of the patient. For example it does not interfere with sleeping. Furthermore, the main apparatus, that of FIGS. 1 and 2, may be in place for at most a month, marketedly less than the prior art equipment. Furthermore, the equipment may in many cases be removed immediately subsequent to the operation if CMT techniques show that the pelvic girdle has been well positioned and the surgeon believes that the artificial joints 52 will hold the pelvic girdle in its corrected position.

The apparatus of the present invention may be made of stainless steel but a disadvantage of this is that the stainless steel may interfere with CMT. It is therefore desirable to use X-ray transparent material, for example resins reinforced with graphite or glass fibre.

The invention also provides a method to treat scoliosis. The illustrated equipment is used as follows. First the patient's sacrum is repositioned to the correct anatomical position to restore the symmetry of the patient's pelvic girdle, using the apparatus of FIGS. 1 and 2. The apparatus is positioned as shown in FIG. 3. Once the pelvic girdle has been repositioned the artificial joints of FIG. 4 are positioned as shown in FIG. 6 to maintain that position. In a great number of cases the artificial joint 52, shown in FIG. 4, are sufficient to maintain the correctly positioned pelvic girdle. That is to say, the apparatus of FIGS. 1 and 2, the main apparatus, may be removed as soon as the artificial joints 52 are in position.

The cords 72, and drive member 64, may be installed and tension applied to cords 72 by rotation of the reels 78. In this way, force is applied to the distorted spine so that it does not tend to act against the effects of the joints 52. Typically the cords 72 may be in place for about one year subsequent to the operation.

A great advantage of the apparatus and method of the invention is that it is possible to treat children as young as 8 years old. The prior art, in general, has only been able to treat children of 12 years old and above. This is because the prior art apparatus tends to inhibit growth and to disturb the vertebrae by fusing of the spine. However, the present apparatus is in place very briefly and the artificial joints 52 and cords 72 have no effect on the growth of the spine. Changing the tensioning of the cords 72 is an easy matter.

Although the forgoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

We claim:

1. Apparatus to treat scoliosis comprising:

a pair of longitudinal struts each strut having opposed ends;

means to adjust the separation of said struts;

a cross member extending between said struts and pivotally mount to each strut, the cross member having opposed ends;

a sub-frame, pivotally attached to the cross member;

means adapted to be received in the pelvic girdle to secure said apparatus to a patient's pelvic girdle, said means being mounted on said sub-frame;

means to pivot said cross member relative to said longitudinal struts to move said struts and thus move the patient's sacrum towards the innominate bones.

2. Apparatus as claimed in claim 1 in which the means to adjust separation of said struts comprises turnbuckles attached adjacent each end of the struts.

3. Apparatus as claimed in claim 1 in which the cross member has a plurality of openings adjacent each end;

pins in said longitudinal struts received in said openings to allow pivoting of said cross member relative to said longitudinal struts.

4. Apparatus as claimed in claim 3 including means to adjust the longitudinal position of said pins in said struts.

5. Apparatus as claimed in claim 1 in which the means to pivot said cross member relative to said longitudinal struts comprises a worm-wheel mounted on said cross member by pivotal joints;

a drive screw for said worm-wheel mounted on said cross member to engage said worm-wheel;

whereby rotation of said drive screw rotates said worm-wheel to pivot said sub-frame to move said longitudinal struts and thus the pelvic girdle.

6. Apparatus as claimed in claim 1 including a threaded housing on each longitudinal strut, above said cross member;

a threaded member received by each threaded housing and extending to engage said cross member, whereby rotation of the threaded members in its respective housing moves the cross member relative to the longitudinal members.

7. Apparatus as claimed in claim 6 in which each threaded member is provided with a ball-joint;

a channel formed in said cross member to receive said ball-joints.

* * * * *